United States Patent [19]

He et al.

[11] Patent Number: 6,106,829
[45] Date of Patent: *Aug. 22, 2000

[54] HUMAN PROSTATIC SPECIFIC REDUCTASE

[75] Inventors: Wei Wu He, Columbia; Paul S. Meissner, Barnesville; Peter L. Hudson, Germantown; Craig A. Rosen, Laytonsville, all of Md.

[73] Assignee: Human Genome Sciences, Inc., Rockville, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/875,273

[22] PCT Filed: Jan. 20, 1995

[86] PCT No.: PCT/US95/01827

§ 371 Date: Oct. 16, 1997

§ 102(e) Date: Oct. 16, 1997

[87] PCT Pub. No.: WO96/22360

PCT Pub. Date: Jul. 25, 1996

[51] Int. Cl.[7] .............................. C12N 9/02; C12N 15/53; A61K 38/44; C07K 14/47
[52] U.S. Cl. ..................... 424/94.4; 435/189; 530/350; 536/23.2
[58] Field of Search ........................... 435/189; 530/350; 424/94.4; 536/23.2

[56] References Cited

U.S. PATENT DOCUMENTS 4,800,159  1/1989  Mullis et al. ..................... 435/172.3
5,420,245  5/1995  Brown et al. ..................... 560/328

OTHER PUBLICATIONS

Riegman, P.H.J. et al., Biochemical and Biophysical Research Communications 155:181–188 (1988).
Israeli, R.S. et al., Cancer Research 53:227–230 (1993).
Israeli, R.S. et al., Cancer Research 54:6306–6310 (1994).
Deguchi, T. et al., Cancer Research 53:5350–5354 (1993).
Matoba, R. et al., Gene 146:199–270 (1994).
Matoba, Genbank Entry D17020, Dec. 1, 1994.
Lewin, "Genes V" (Oxford University Press), p. 648 (1994).
Nierman, W.C. et. al., ATCC/NIH Repository Cataglogue of Human and Mouse DNA Probes and Libraries, 1–58 (1994).
Moreno et al., Detection of Hematogenous Micrometastasis in Patients with Prostate Cancer, 6110–6112 (1992).

*Primary Examiner*—Rebecca E. Prouty
*Attorney, Agent, or Firm*—Human Genome Sciences, Inc.

[57] ABSTRACT

A human prostatic specific reductase polypeptide and polynucleotides encoding such polypeptide and a procedure for producing such polypeptide by recombinant techniques is disclosed. Also disclosed are methods for utilizing such polynucleotides as a diagnostic marker for prostate cancer and as an agent to determine if the prostate cancer has metastasized. Also disclosed are antibodies specific to the prostatic specific reductase polypeptide which may be used to target prostate cancer cells and be used as part of a prostate cancer vaccine. Methods of screening for agonists and antagonists for the polypeptide and therapeutic uses of the antagonists are also dislcosed.

16 Claims, 4 Drawing Sheets

FIG. IA

```
  1  CCGGCAGAGATGGTTGAGCTCATGTTCCCGCTGTTCTCCTCCTTCTGCCCTTCCTTCTG
  1                M  V  E  L  M  F  P  L  L  L  L  L  P  F  L  L
 61  TATATGGCTGCGCCCCAAATCAGGAAAATGCTGTCCAGTGGGTGTACATCAACTGTT
 18   Y  M  A  A  P  Q  I  R  K  M  L  S  S  G  V  C  T  S  T  V
121  CAGCTTCCTGGAAAGTAGTCGGTCACAGGAGCTAATACAGGTATCGGGAAGGAGACA
 38   Q  L  P  G  K  V  V  V  T  G  A  N  T  G  I  G  K  E  T
181  GCCAAAGAGCTGGCTCAGAGAGGCTCGAGTATATTTAGCTTGCCCGGGATGTGGAAAAG
 58   A  K  E  L  A  Q  R  G  A  R  V  Y  L  A  C  R  D  V  E  K
241  GGGGAATTGGTGGCCAAAGAGATCCAGACCACGAACCAGCAGGTGTTGGTGCGG
 78   G  E  L  V  A  K  E  I  Q  T  T  G  N  Q  Q  V  L  V  R
301  AAACTGGACCTGTCTGATACTAAGTCTATTCGAGCTTGGGCTTCTTAGCTGAG
 98   K  L  D  L  S  D  T  K  S  I  R  A  W  A  K  G  F  L  A  E
361  GAAAAGCACCTCCACGTTTGGATCAACAATGCAGGAGTGATGTGTCCGTACTCGAAG
118   E  K  H  L  H  V  W  I  N  N  A  G  V  M  M  C  P  Y  S  K
421  ACAGGAGATGGCTTTGAGAGAAACTAAAGGAATCAGCCCCATCAAGGATAGTAAATGTGTCTTCC
138   T  A  D  G  F  E  M  H  I  G  V  N  H  L  G  H  F  L  L  T
481  CATCTGCTGCTAGAGAAACTAAAGGAATCAGCCCCATCAAGGATAGTAAATGTGTCTTCC
158   H  L  L  E  K  L  K  E  S  A  P  S  R  I  V  N  V  S  S
541  CTCGCACATCACCTGGAAGATCCACTTCCATAACCTGCAGGGCGAGAAATTCTACAAT
178   L  A  H  H  L  G  R  I  H  F  H  N  L  Q  G  E  K  F  Y  N
601  GCAGGCCTGGCCTACTGTCACAGCAAGCTAGCCAACATCCTCTTCACCCAGGAACTGGCC
198   A  G  L  A  Y  C  H  S  K  L  A  N  I  L  F  T  Q  E  L  A
661  CGGAGACTAAAAGGCTCTGGCGTTACGACGTATTCTGTACACCCTGGCACAGTCCAATCT
218   R  R  L  K  G  S  G  V  T  T  Y  S  V  H  P  G  T  V  Q  S
```

FIG. 1B

```
 721  GAACTGGTTCGGCACTCATCTTTCATGAGATGTGGTGGCTTTTCTCCTTTTCATC
 238   E  L  V  R  H  S  S  F  M  R  M  W  W  L  F  S  F  F  I
 781  AAGACTCCTCAGCAGGAGCCCAGGCTCACTGTGCCTTAACAGAAGGTCTTGAG
 258   K  T  P  Q  Q  G  A  Q  T  R  L  H  C  A  L  T  E  G  L  E
 841  ATTCTAAGTGGGAATCATTTCAGTGACTGTCATGTGGCTGTCTGCCAAGCTCGT
 278   I  L  S  G  N  H  F  S  D  C  H  V  A  W  V  S  A  Q  A  R
 901  AATGAGACTATAGCAAGGCGGCTCATTGTGACCTGTTGGGCCTCCCAATAG
 298   N  E  T  I  A  R  R  L  W  D  V  I  V  T  C  W  A  S  Q  *
 961  ACTAACAGGCAGTGCCAGTTGGACCCAAGAGAGACTGCAGCAGACTACAGTACTTCT
1021  TGTCAAATGATTCTTCAAGGTTTTCAAACCTTTAGCACAAAGAGAGCAAAACCTT
1081  CCAGCC
```

Nucleotide and amino acid sequences of prostatic specific reductase (PSR).

FIG. 2A

```
1    M - - - - - - - - - - A A P Q I R K M L S G V C T S T V Q L   PSR
1    M - - - - - - - - - - - - - - - - - - - - - - - - - - D L   Oxidoreductase
1    M L L A A A F L V A F V L L L Y M V S P L I S P K P L A L   fvt1

22   P G K V V V T G A N T G I G K E T A K E L A Q R G A R V Y   PSR
4    T G R R A V V T G G A S G L G A E T V R A L A A A G A E V T   Oxidoreductase
31   P G A H V V V T G G S S G F G K C I A I E C Y K Q G A F I T   fvt1

52   L A C R D V E K G E L V A K E I Q - - T T T G N Q Q V L V R   PSR
34   V A T R R P L S A E P L V Q E L A - - A A G G R V T A E       Oxidoreductase
61   L V A R N E D K L L Q A K K E I E M H S I N D K Q V L C I     fvt1

80   K L D L S D T - K S I R A W A K G F L A E E K H L H V W I N   PSR
62   A L D L S D P - A S V E S F A R A W R G - - P L D I L V A     Oxidoreductase
91   S V D V S Q D Y N Q V E N V I K Q A Q E K L G P V D M L V N   fvt1

109  N A G V M M C P - Y S K - T A D G F E M H I G V N H L G H F   PSR
88   N A G I M A L P - T R T L A P N G W E M Q L A T N Y L G H F   Oxidoreductase
121  C A G M A V S G K F E D L E V S T F E R L M S I N Y L G S V   fvt1

137  L T H L L E K L K E S A P S R I V N V S S L A H H L G R       PSR
117  A L A T G L H A A L R D A G S A R I V V S S G A H L D A P     Oxidoreductase
151  Y P S R A V I T T M K E R R V G R I V F V S S Q A G Q L G L   fvt1
```

FIG. 2B

```
167 I H F - - - - - - - - - - - - H N L Q - G E K F Y N A G   PSR
147 F D F - - - - - - - - - - - - - E D A H F A R R P Y D P W   Oxidoreductase
181 F G F T A Y S A S K F A I R G L A E A L Q M E V K P Y N V Y   fvt1

182 L - - A Y C H S K L A N I L F T Q E L A R R L K G S G V - -   PSR
163 V - - A Y G Q S K A A D V L F T V G - A R R W A A D G I - -   Oxidoreductase
211 I T V A Y P P D T D T P G F A E E N R T K P L E T R L I S E   fvt1

208 T T Y S V H P G T V Q S E L V R H - - S S F M R W M W L F -   PSR
188 T V N A L N P G Y I L T R L Q R H V D D E T M R - - - A F -   Oxidoreductase
241 T S V C K P E Q V A K Q I V K D A I Q G N F N - - - - - - -   fvt1

236 S F - - - - - - - - - - - F I K T P Q G A Q T R L H C A -   PSR
214 G V M D D Q G N V - K P L P Y Y K T P E Q A A T S V L L A -   Oxidoreductase
265 S L G S D G Y M L S A L T C G M A P V T S I T E G L Q Q V -   fvt1

254 L T E G L E I L S G N H F S D C H V A W - - - - - - - - - -   PSR
243 A S P L L K G V T G R Y E E D N Q E A R T V Q G Q E D Q P G   Oxidoreductase
295 V T M G L F R T I A L F Y L G S F D S I V R R C M M Q R E K   fvt1

274 - V S A Q A R N E T I A R R L W D V I V T C W A S Q - - - -   PSR
273 G V A A H A L D P E A A D R L W E Y G T D A L - R A A - - -   Oxidoreductase
325 S E N A D - - - - - - - - - - - - - - - - - - - K T A - - -   fvt1
```

Alignment of human PSR with Streptomyces Oxidoreductase (Oxidoreductase) and human follocular variant translocation gene (fvt1).

HUMAN PROSTATIC SPECIFIC REDUCTASE

This invention relates to newly identified polynucleotides, polypeptides encoded by such polynucleotides, and the use of such polynucleotides and polypeptides as part of a diagnostic assay for detecting the presence of prostate cancer and prostate cancer metastases. The polynucleotides and polypeptides of the present invention are human prostatic specific reductase, and are sometimes hereinafter referred to as "PSR".

Carcinoma of the prostate has long been regarded as an unpredictable disorder which makes sound therapeutic decisions in evaluating the results of different types of treatment very difficult. Prostate cancer is unique among the potentially lethal human malignancies in that there is a wide discrepancy between the high prevalence of histologic changes recognizable as cancer and the much lower prevalence of clinical disease.

The concept that adenocarcinoma of the prostate exists in a latent and a clinical form is supported by epidemiologic, pathologic and clinical evidence. Although these divergent manifestations of prostate cancer have come in architectural and cytologic features, they can be distinguished from each other to some degree by differences in certain pathologic features, such as the volume, grade, and invasiveness of the lesion.

Prostate cancer has become the most common cancer among American men, and only lung cancer is responsible for more cancer deaths (Boring, C. C., Cancer Statistics, 41:19–36 (1991)). The age specific mortality rate has slowly increased over the past 50 years and in black American men is nearly double the rate found in white men (Carter, H. B., Prostate, 16:39–48 (1990)). Prostate cancer is responsible for nearly three percent of all deaths in men over the age of 55 years (Seidman, H., et al., Probabilities of Eventually Developing or Dying of Cancer-United States, 35:36–56 (1985)). Since the incidence of prostate cancer increases more rapidly with age than any other cancer, and the average age of American men is rising, the number of patients with prostate cancer is expected to increase dramatically over the next decade.

Approximately 30% of men with prostate cancer have distant metastases at the time of diagnosis (Schmidt, J. D., et al., J. Urol., 136:416–421 (1986)). Despite the impressive symptomatic response of metastases to hormonal manipulation (androgen deprivation), the survival rate for these patients is dismal: the median duration of survival is less than three years (Eyar, D. P., Urologic Pathology: The Prostate, Philadelphia, Pa., Lea and Febiger, 241–267 (1977)). By five years, over 75% and by ten years, more than 90% of these patients die of their cancer rather than with it (Silverberg, E., Cancer, 60:692–717 (1987) (Suppl.)).

The problem with prostate cancer is that many forms of prostate cancer are latent, in other words, are difficult to detect. Approximately 30% of the men over the age of 50 years who have no clinical evidence of prostate cancer harbor foci of cancer within the prostate (McNeal, J. E., et al., Lancet January, 11:60–63 (1986)). This remarkably high prevalence of prostate cancer at autopsy, seen in no other organ, makes it the most common malignancy in human beings (Dhom, G., J. Cancer Res. Clin. Oncol., 106:210–218 (1983)). There is strong support for the concept of multi-step process in the pathogenesis of prostate cancer in which latent cancers progress through some but not all of the steps necessary for full malignant expression (Utter, H. B., et al., J. Urol., 143:742–746 (1990).

There are a variety of techniques for early detection and characteristics of prostate cancers, however, none of them are devoid of any problems. Prostate cancer is a notoriously silent disease with few early symptoms. Symptoms associated with bladder outlet obstruction are commonly present in men over the age of 50 years and are often ascribed to benign prostatic hyperplasia (BPH).

Digital rectal examination (DRE) traditionally has been considered the most accurate test for the detection of prostate cancer. DRE has been demonstrated to be more sensitive, more specific, and to have a greater efficiency than a variety of laboratory tests available, however, few of these laboratory tests are still in clinical use today (Guinan, P., et al., N. Engl. J. Med., 303:499–503 (1980)). DRE detects cancer relatively late, and there is only a weak correlation between the size of the cancer estimated by DRE and the actual volume of cancer present. The most serious limitation of DRE is its lack of sensitivity (false-negative results). For example, approximately 10% to 20% of transurethral resections performed for benign prostatic hypertrophy in patients with no palpable abnormalities suggestive of cancer uncover an incidental cancer of the prostate. DRE detected only 12 of 22 cancers found in a screening study, while transrectal ultrasonography (TRUS) found 20 (Lee, F., et al., Radiology, 168:389–394 (1988)). Thus, DRE is relatively insensitive and nonspecific. Cancers detected by palpation are relatively large, late in their development and no longer curable, and some are very small, such that they are clinically unimportant cancers.

Patients having prostate cancer have an elevated prostate-specific antigen level. Cancer was detected in 26% of the men with a PSA level of 4.0 to 10.0 ng/ml. Serum PSA levels have been shown to correlate generally with the volume, clinical stage, and pathologic stage of prostate cancer, although there is a wide range of PSA values associated with any given volume or stage (Hudson, M. A., J. Urol., 142:1011–1017 (1989)). PSA, however, is not predictive of the features of the cancer in the individual patient. If the level of PSA is greater than 10.0 ng/ml, 57% to 92% of the patients will have locally advanced cancer. Therefore, while more specific, using a PSA level higher than 10 ng/ml may not offer an effective technique for early detection. There are other theoretical limitations to the use of this serum marker for early detection. A normal serum PSA level does not exclude the diagnosis of cancer. False-negative results are common, and a third of men treated with radioprostatectomy for prostate cancer have a normal serum PSA level. False-positive results are also common since PSA levels are often elevated in men with common benign conditions, such as BPH or prostatitis. In summary, PSA levels have proved to be extremely useful in the early detection of prostate cancer, especially when combined with DRE or TRUS. A PSA level detection, however, must be used in combination with DRE or TRUS in order to be sure that what is present is cancer and not BPH or prostatitis.

The introduction of TRUS has provided physicians with an effective way to see the internal anatomy and pathology of the prostate gland. TRUS has been used to screen for prostate cancer in several large series and has consistently been shown to increase detection when compared with DRE. TRUS is performed by taking a sonograph of the pelvic area and perhaps the most important use of TRUS in the early detection of prostate cancer is as a guide for directed needle biopsies of the prostate (Lee, F., et al., Radiology, 170:609–615 (1989)).

In accordance with one aspect of the present invention there is provided a method of and products for diagnosing prostate cancer metastases by determining the presence of specific nucleic acid sequences in a sample derived from a host.

In accordance with another aspect of the present invention, there is provided a method of and products for diagnosing a prostate disorder by determining an altered level of PSR protein in a biological sample derived from a host, whereby an elevated level of PSR protein indicates a prostate disorder diagnosis.

In accordance with another aspect of the present invention, there is also provided nucleic acid probes comprising nucleic acid molecules of sufficient length to specifically hybridize to the prostatic specific reductase genes and polypeptides of the present invention.

In accordance with a further aspect of the present invention, there are provided novel polypeptides which are prostatic specific reductase polypeptides, as well as biologically active and diagnostically or therapeutically useful fragments, analogs and derivatives thereof.

In accordance with another aspect of the present invention, there are provided isolated nucleic acid molecules encoding human PSR proteins, including mRNAs, DNAs, cDNAs, genomic DNAs, as well as biologically active and diagnostically or therapeutically useful fragments, analogs, and derivatives thereof.

In accordance with yet a further aspect of the present invention, there is provided a process for producing such polypeptide by recombinant techniques comprising culturing recombinant prokaryotic and/or eukaryotic host cells, containing human prostatic specific reductase nucleic acid sequences, under conditions promoting expression of said proteins and subsequent recovery of said proteins.

In accordance with yet a further aspect of the present invention, there are provided antibodies specific to such polypeptides.

In accordance with another aspect of the present invention, there are provided processes for using the PSR polypeptides of the present invention to screen for compounds, for example, antagonists and/or agonists and antibodies which interact with the polypeptides.

In accordance with yet another aspect of the present invention, there are provided antagonists to such polypeptides, which may be used to inhibit the action of such polypeptides, for example, in the treatment of prostate cancer.

These and other aspects of the present invention should be apparent to those skilled in the art from the teachings herein.

The following drawings are illustrative of embodiments of the invention and are not meant to limit the scope of the invention as encompassed by the claims.

FIGS. 1A and 1B show the cDNA sequence and the corresponding deduced amino acid sequence of the PSR polypeptide. The standard one-letter abbreviations for amino acids is used.

FIGS. 2A and 2B show the homology of PSR to other reductases.

The boxed amino acids are those which correspond exactly between the polypeptides.

In accordance with an aspect of the present invention there is provided a diagnostic assay for detecting micrometastases of prostate cancer in a host. While applicant does not wish to limit the reasoning of the present invention to any specific scientific theory, it is believed that the presence of mRNA encoding PSR in cells of the host, other than those derived from the prostate, is indicative of prostate cancer metastases. This is true because, while the PSR genes are found in all cells of the body, their transcription to mRNA and expression of the encoded polypeptide is limited to the prostate in normal individuals. However, if a prostate cancer is present, prostate cancer cells migrate from the cancer to other cells, such that these other cells are now actively transcribing and expressing the PSR genes and the mRNA is present. It is the detection of this mRNA or expressed protein in cells, other than those derived from the prostate, which is indicative of metastases of prostate cancer.

In such a diagnostic assay, a nucleic acid sequence in a sample derived from a tissue other than the prostate is amplified and detected. The sample contains a nucleic acid or a mixture of nucleic acids, at least one of which is suspected of containing the sequence coding for PSR polypeptide. Thus, for example, in a form of an assay for determining the presence of a specific mRNA in cells, initially RNA is isolated from the cells.

There are numerous methods, which are well known in the art, for detecting the presence of a specific nucleic acid sequence in a sample obtained from cells, such as from blood, urine, saliva, tissue biopsy, and autopsy material. The use of such assays for detecting mRNA transcribed from the PSR gene in a sample obtained from cells derived from other than the prostate is well within the scope of those skilled in the art from the teachings herein.

The isolation of mRNA comprises isolating total cellular RNA by disrupting a cell and performing differential centrifugation. Once the total RNA is isolated, mRNA is isolated by making use of the adenine nucleotide residues known to those skilled in the art as a poly (A) tail found on virtually every eukaryotic mRNA molecule at the 3' end thereof. Oligonucleotides composed of only deoxythymidine [oligo(dT)] are linked to cellulose and the oligo(dT)-cellulose packed into small columns. When a preparation of total cellular RNA is passed through such a column, the mRNA molecules bind to the oligo(dT) by the poly(A)tails while the rest of the RNA flows through the column. The bound mRNAs are then eluted from the column and collected.

One example of detecting mRNA encoding for a specific protein, for example PSR, comprises screening the collected mRNAs with gene specific oligonucleotide probes which have been custom designed to hybridize to the mRNA to be detected. Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product.

Another method for detecting a specific mRNA sequence utilizes the polymerase chain reaction (PCR) in conjunction with reverse transcriptase. PCR is a very powerful method for the specific amplification of DNA or RNA stretches (Saiki et al., Nature, 234:163–166 (1986)). One application of this technology is in nucleic acid probe technology to bring up nucleic acid sequences present in low copy numbers to a detectable level. Numerous diagnostic and scientific applications of this method have been described by H. A. Erlich (ed.) in PCR Technology-Principles and Applications for DNA Amplification, Stockton Press, USA, 1989, and by M. A. Inis (ed.) in PCR Protocols, Academic Press, San Diego, USA, 1990.

RT-PRC is a combination of PCR with an enzyme called reverse transcriptase. Reverse transcriptase is an enzyme which produces cDNA molecules from corresponding mRNA molecules. This is important since PCR amplifies nucleic acid molecules, particularly DNA, and this DNA may be produced from the mRNA separated from the body sample derived from the host.

An example of an RT-PCR diagnostic assay involves removing a sample from a tissue of a host. Such a sample will be from a tissue, other than the prostate, extracting total RNA from the sample, performing PSR RT-PCR of total RNA and electrophoresing on an agarose gel the PCR products. The oligonucleotide primers used for RT-PCR are between 16 and 50 nucleotide bases in length and preferably between 16 and 30 nucleotide bases in length. Any segment of the PSR mRNA sequence may be used to generate the oligonucleotides. In this manner, once the sequences aer amplified using PCR, genomic DNA may be distinguished from PSR mRNA since different size bands will appear after electrophoresis on a 1.2% agarose gel. The presence of genomic DNA, an approximately 1.2 kb band, is a reading which is a negative indication concerning metastases. However, a much smaller band indicates mRNA is present which means the PSR gene is being actively transcribed which in turn indicates prostate cells are circulating in the blood and possibly metastisizing.

Another example for detecting a specific RNA in a sample involves generating a cDNA molecule which corresponds to the mRNA to be detected by the use of reverse transcriptase and, thereafter, cloning the cDNA molecule into a vector to prepare a library. Such a method involves transforming bacterial cells with the plasmid and spreading the cells onto the surface on an agar plate that contains nutrients for growth and appropriate antibiotics for selection. In this manner all of the mRNAs from the collected fraction are transformed into the bacteria and plated out into individual colonies.

The mRNA may be detected from the library in a variety of methods. For example nucleic acid probes may be used to locate clones carrying a desired DNA sequence. In such a method a replica of the library is prepared on nitrocellulose filters. This process transfers a portion of each colony to the nitrocellulose. Screening is carried out by incubating these nitrocellulose replicas with a nucleic acid probe with an antibody which is specific to the cDNA corresponding to the mRNA to be detected.

The presence of mRNA transcribed from PSR in cells derived from other than the prostate may also be determined by use of an assay which detects the expression product of such gene. Thus, for example, such an assay involves producing cDNA from the mRNA contained in the sample and then determining the presence of a specific mRNA by detecting the expression product of the cDNA produced therefrom.

In such a method cDNAs are identified by searching for their gene products in bacteria after cloning the cDNA into appropriately constructed plasmids termed expression vectors. cDNAs are inserted into these vectors within regions that promote their expression in *E. Coli*. Regulatable bacterial promoters are used. Proteins may be expressed as fusion proteins in which amino acids from a prokaryotic protein are incorporated at one end of the eukaryotic protein. Fusion proteins are more stable than corresponding eukaryotic protein in bacteria and are therefore produced at higher levels.

Another method to detect the mRNA sequence is to locate clones that express a desired protein and assay for the function of the protein, for example PSR. Radioactively labelled substrate for PSR may be used as a probe to identify clones expressing proteins that are able to associate with the substrate in vitro.

The cloned genes may also be identified by functional assay in eukaryotic cells. This technique allows direct physical selection of cells expressing the cDNA of interest, and this cDNA can be recovered directly from the cells. Mammalian genes can also be isolated by genetic selection for their function in recipient cells.

The presence of active transcription from the PSR gene to produce corresponding mRNA in cells other than the prostate is an indication of the presence of a prostate cancer which has metastasized, since prostate cancer cells are migrating from the prostate into the general circulation. Accordingly, this phenomenon may have important clinical implications since the method of treating a localized, as opposed to a metastasized, tumor is entirely different. The presence of PSR mRNA in the peripheral venous blood is an indication of metastases.

The assays described above may also be used to test whether bone marrow preserved before chemotherapy is contaminated with micrometastases of a prostate cancer cell. In the assay, blood cells from the bone marrow are isolated and treated as described above, this method allows one to determine whether preserved bone marrow is still viable for transplantation after chemotherapy.

This invention is also related to use of the PSR genes as a diagnostic. For example, some diseases result form inherited defective genes. A mutation in the genes at the DNA level may be detected by a variety of techniques. Nucleic acids used for diagnosis (genomic DNA, mRNA, etc.) may be obtained from a patient's cells, other than from the prostate, such as from blood, urine, saliva, tissue biopsy and autopsy material. The genomic DNA may be used directly for detection or may be amplified enzymatically by using PCR prior to analysis. RNA or cDNA may also be used for the same purpose. As an example, PCR primers complementary to the nucleic acid of the instant invention can be used to identify and analyze PSR gene mutations. For example, deletions and insertions can be detected by a change in size of the amplified product in comparison to the normal genotype. Point mutations can be identified by hybridizing amplified DNA to radiolabelled PSR gene RNA or, alternatively, radiolabelled antisense DNA sequences. Perfectly matched sequences can be distinguished from mismatched duplexes by RNase A digestion or by differences in melting temperatures.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabelled nucleotides or by automatic sequencing procedures with fluorescent-tags.

Genetic testing based on DNA sequence differences may be achieved by detection of alteration in electrophoretic mobility of DNA fragments and gels with or without denaturing agents. Small sequence deletions and insertions can be visualized by high-resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers, et al., *Science*, 230:1242 (1985)). In addition, sequence alterations, in particular small deletions, may be detected as changes in the migration pattern of DNA.

Sequence changes at specific locations may also be revealed by nuclease protection assays, such as RNase and S1 protection or the chemical cleavage method (e.g., Cotton, et al., *PNAS, USA*, 85:4397–4401 (1985)).

Thus, the detection of the specific DNA sequence may be achieved by methods such as hybridization, RNase protection, chemical cleavage, direct DNA sequencing, or the use of restriction enzymes (e.g., Restriction Fragment Length Polymorphisms (RFLP)) and Southern blotting.

In accordance with another aspect of the present invention, there is provided a method of diagnosing a disorder of the prostate, for example cancer, by determining atypical levels of PSR products in a biological sample, derived from a tissue other than the prostate. Assays used to detect levels of PSR proteins in a sample derived from a host are well-known to those with skill in the art and include radioimmunoassays, competitive-binding assays, western blot analysis, ELISA assays and "sandwich" assays. A biological sample may include, but is not limited to, tissue extracts, cell samples or biological fluids, however, a biological sample specifically does not include tissue or cells of the prostate. An ELISA assay (Coligan, et al., *Current Protocols in Immunology*, 1(2), Chapter 6, 1991) initially comprises preparing an antibody specific to PSR proteins, preferably a monoclonal antibody. In addition, a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g., a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any PSR proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to PSR proteins. Unattached reporter antibody is then washed out. Peroxidase substrates are then added to the dish and the amount of color developed in a given time period is a measurement of the amount of PSR proteins present in a given volume of patient sample when compared against a standard curve.

A competition assay may be employed where an antibody specific to PSR proteins are attached to a solid support and labeled PSR proteins and a sample derived from the host are passed over the solid support and the amount of label detected, for example, by liquid scintillation chromatography, can be correlated to a quantity of PSR proteins in the sample.

A "sandwich" assay is similar to an ELISA assay. In a "sandwich" assay, PSR proteins are passed over a solid support and bind to antibody attached to the solid support. A second antibody is then bound to the PSR proteins. A third antibody which is labeled and is specific to the second antibody, is then passed over the solid support and binds to the second antibody and an amount can then be quantified.

In alternative methods, labeled antibodies to PSR proteins are used. In a one-step assay, the target molecule, if it is present, is immobilized and incubated with a labeled antibody. The labeled antibody binds to the immobilized target molecule. After washing to remove the unbound molecules, the sample is assayed for the presence of the label. In a two-step assay, immobilized target molecule is incubated with an unlabeled antibody. The target molecule-labeled antibody complex, if present, is then bound to a second, labeled antibody that is specific for the unlabeled antibody. The sample is washed and assayed for the presence of the label.

The choice of marker used to label the antibodies will vary depending upon the application. However, the choice of marker is readily determinable to one skilled in the art. These labeled antibodies may be used in immunoassays as well as in histological applications to detect the presence of the proteins. The labeled antibodies may be polyclonal or monoclonal.

Such antibodies specific to PSR, for example, anti-idiotypic antibodies, can be used as a prostate cancer vaccine since the antibodies prevent the action of PSR by binding tightly thereto, and, therefore, prevent or eliminate the viability of prostate cancer cells.

The antibodies may also be used to target prostate cancer cells, for example, in a method of homing interaction agents which, when contacting prostate cancer cells, destroy them. This is true since the antibodies are specific for PSR which is primarily expressed in the prostate, and a linking of the interaction agent to the antibody would cause the interaction agent to be carried directly to the prostate.

Antibodies of this type may also be used to do in vivo imaging, for example, by labeling the antibodies to facilitate scanning of the pelvic area and the prostate. One method for imaging comprises contacting any tumor cells of the prostate to be imaged with an anti-PSR antibody labeled with a detectable marker. The method is performed under conditions such that the labeled antibody binds to the PSR. In a specific example, the antibodies interact with the prostate, for example, prostate cancer cells, and fluoresce upon such contact such that imaging and visibility of the prostate is enhanced to allow a determination of the diseased or non-diseased state of the prostate.

To determine if the amount of PSR polypeptide is elevated, the methods described above may be performed on a number of hosts who are known to be healthy, i.e. do not have a disorder of the prostate. An average level of PSR polypeptide could then be determined whic will act as a standard against which levels of PSR polypeptides can be measured for the identification of atypical amounts of PSR polypeptides in vivo.

In accordance with another aspect of the present invention, there is provided an isolated nucleic acid (polynucleotide) which encodes for the mature polypeptide having the deduced amino acid sequence of SEQ ID No. 2 or for the mature polypeptide encoded by the cDNA of the clone deposited as ATCC Deposit No. 75913 on Oct. 11, 1994.

The polynucleotide of this invention was discovered in a cDNA library derived from a human prostate. The PSR gene is primarily expressed in the prostate and has not been found in any other human cDNA tissue libraries screened by the inventors (see Table 1 below). PSR contains an open reading frame encoding a protein of 316 amino acid residues.

TABLE 1

Identification of PSR as a Prostatic Specific Gene

|  | Normal Prostate | Stage B2 Cancer | Stage C Cancer | All other tissues |
|---|---|---|---|---|
| PSA | 4 | 7 | 14 | 0 |
| PAP | 13 | 1 | 34 | 0 |
| PSR | 0 | 3 | 7 | 0 |
| Total Clones Sequenced | 4472 | 956 | 3397 | 275,261 |

As shown in Table 1, three prostatic cDNA libraries were constructed and large numbers of clones from these three libraries were sequenced. The clones identified from these libraries were compared with a data base which contains 275,261 independent cDNA clone identifications obtained from more than 300 human cDNA libraries other than human prostatic cDNA libraries. As illustrated in the table, human prostatic Specific Antigen (PSA) was identified 4 times in the normal human prostate library, 7 times in a stage B2 human prostate cancer library and 14 times in a stage C human prostate cancer library. Human prostatic acid phosphatase (PAP) was identified 13 times in a normal human prostate library, once in a stage B2 human prostate cancer library and 14 times in a stage C prostate cancer library. The prostatic specific reductase of this invention was identified 3 times in the stage B2 human prostate cancer library and 7 times in the stage C prostate cancer library, and most notably was not identified at all in the normal human prostate library or from libraries derived from non-prostate tissues, indicating its importance as a marker for prostate disorders.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID No. 2 or that of the deposited clone or may be a different coding sequence which coding sequence, as a result of the redundancy or degeneracy of the genetic code, encodes the same mature polypeptide as the DNA of SEQ ID No. 1 or the deposited cDNA.

The polynucleotide which encodes for the mature polypeptide of SEQ ID No. 2 or for the mature polypeptide encoded by the deposited cDNA may include: only the coding sequence for the mature polypeptide or the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide or which includes additional coding and/or non-coding sequence.

The present invention further relates to variants of the hereinabove described polynucleotides which encode for fragments, analogs and derivatives of the polypeptide having the deduced amino acid sequence of SEQ ID No. 2 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in SEQ ID No. 2 or the same mature polypeptide encoded by the cDNA of the deposited clone as well as variants of such polynucleotides which variants encode for a fragment, derivative or analog of the polypeptide of SEQ ID No. 2 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in SEQ ID No. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. An example of a marker sequence is a hexa-histidine tag which may be supplied by a vector, preferably a pQE-9 vector, which provides for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides . As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of SEQ ID No. 1 or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a PSR polypeptide which has the deduced amino acid sequence of SEQ ID No. 2 or which has the amino acid sequence encoded by the deposited cDNA, as well as fragments, analogs and derivatives of such polypeptide.

The terms "fragment," "derivative" and "analog" when referring to the polypeptide of SEQ ID No. 2 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of SEQ ID No. 2 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the PSR genes. The culture conditions, such as temperature, pH and the like, are those previously used with the host cell selected for expression, and will be apparent to those of ordinarily skill in the art.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Sf 9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, PMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The PSR polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

In accordance with another aspect of the present invention there are provided assays which may be used to screen for therapeutics to inhibit PSR, since PSR is a reductase and may be necessary for the proliferation of the prostate cancer cells. The present invention discloses methods for selecting a therapeutic which forms a complex with PSR with sufficient affinity to prevent the biological action of PSR. The methods include various assays, including competitive assays where the PSR is immobilized to a support, and is contacted with a natural substrate for PSR and a labeled therapeutic either simultaneously or in either consecutive order, and determining whether the therapeutic effectively competes with the natural substrate in a manner sufficient to prevent binding of PSR to its substrate. In another embodiment, the natural substrate is labeled and the therapeutic is unlabeled. In a further embodiment, the substrate is immobilized to a support, and is contacted with both labeled PSR and a therapeutic (or unlabeled PSR and a labeled therapeutic), and it is determined whether the amount of PSR bound to the substrate is reduced in comparison to the assay without the therapeutic added. The PSR may be labeled with the anti-PSR antibodies of the subject invention.

In another example of such a screening assay, there is provided a mammalian cell or membrane preparation expressing the PSR polypeptide incubated with elements which undergo simultaneous oxidation and reduction, for example hydrogen and oxygen which together form water, wherein the hydrogen could be labeled by radioactivity, e.g., tritium, in the presence of the compound to be screened under conditions favoring the oxidation reduction reaction where hydrogen and oxygen form water. The ability of the compound to enhance or block this interaction could then be measured.

Potential antagonists to PSR including antibody, i.e., an anti-idiotypic antibody as described above, or in some cases, an oligonucleotide, which binds to the polypeptide.

Another potential PSR antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix see Lee et al., Nucl. Acids Res., 6:3073

(1979); Cooney et al, Science, 241:456 (1988); and Dervan et al., Science, 251: 1360 (1991)), thereby preventing transcription and the production of PSR. The antisense RNA oligonucleotide hybridizes to the mRNA in vivo and blocks translation of the mRNA molecule into the PSR polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of PSR.

Potential antagonists also include a small molecule which binds to and occupies the active site of the polypeptide thereby making the active site inaccessible to substrate such that normal biological activity is prevented. Examples of small molecules include but are not limited to small peptides or peptide-like molecules.

The antagonists may be employed to treat prostate cancer, since they inhibit the function of PSR which is necessary for the viability of the prostate cancer cells. The antagonists may be employed in a composition with a pharmaceutically acceptable carrier, e.g., as hereinafter described.

Fragments of the full length PSR gene may be used as a hybridization probe for a cDNA library to isolate the full length PSR gene and to isolate other genes which have a high sequence similarity to the PSR gene or similar biological activity. Probes of this type can be, for example, between 20 and 2000 base pairs. Preferably, however, the probes have between 30 and 50 bases. The probe may also be used to identify a cDNA clone corresponding to a full length transcript and a genomic clone or clones that contain the complete PSR gene including regulatory and promotor regions, exons, and introns. An example of a screen comprises isolating the coding region of the PSR gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The PSR polypeptides or agonists or antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal, intra-anal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The PSR polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Determination of PSR Gene Transcription in Tissue Other Than Prostate

To assess the presence or absence of active transcription of PSR mRNA, approximately 6 ml of venous blood is obtained with a standard venipuncture technique using heparinized tubes. Whole blood is mixed with an equal volume of phosphate buffered saline, which is then layered over 8 ml of Ficoll (Pharmacia, Uppsala, Sweden) in a 15-ml polystyrene tube. The gradient is centrifuged at 1800×g for 20 min at 5° C. The lymphocyte and granulocyte layer (approximately 5 ml) is carefully aspirated and rediluted up to 50 ml with phosphate-buffered saline in a 50-ml tube, which is centrifuged again at 1800×g for 20 min. at 5° C. The supernatant is discarded and the pellet containing nucleated cells is used for RNA extraction using the RNazole B method as described by the manufacturer (Tel-Test Inc., Friendswood, Tex.).

Two oligonucleotide primers are employed to amplify the PSR nucleotide sequence present in the sample: the 5' primer is 5' AAGAGATCCAGACCACGCAGG 3' (SEQ ID No. 3) and the 3' primer is 5' AAGGCACAGTGCAGCCTGGTCT 3' (SEQ ID No. 4). The reverse transcriptase reaction and PCR amplification are performed sequentially without interruption in a Perkin Elmer 9600 PCR machine (Emeryville, Calif.). Four hundred ng total RNA in 20 µl diethylpyrocarbonate-treated water are placed in a 65° C. water bath for 5 min. and then quickly chilled on ice immediately prior to the addition of PCR reagents. The 50-µl total PCR volume consisted of 2.5 units Taq polymerase (Perkin-Elmer). 2 units avian myeloblastosis virus reverse transcriptase (Boehringer Mannheim, Indianapolis, Ind.); 200 µM each of dCTP, dATP, dGTP and dTTP (Perkin Elmer); 18 pM each primer, 10 mM Tris-HCl; 50 mM KCl; and 2 mM $MgCl_2$ (Perkin Elmer). PCR conditions are as follows: cycle 1 is 42° C. for 15 min then 97° C. for 15 s (1 cycle); cycle 2 is 95° C. for 1 min. 60° C. for 1 min, and 72° C. for 30 s (15 cycles); cycle 3 is 95° C. for 1 min. 60° C. for 1 min., and 72° C. for 1 min. (10 cycles); cycle 4 is 95° C. for 1 min., 60° C. for 1 min., and 72° C. for 2 min. (8 cycles); cycle 5 is 72° C. for 15 min. (1 cycle); and the final cycle is a 4° C. hold until sample is taken out of the machine. The 50-µl PCR products are concentrated down to 10 µl with vacuum centrifugation, and the entire sample is then run on a thin 1.2 % Tris-borate-EDTA agarose gel containing ethidium bromide. A 1.2 kb band indicates that genomic DNA is amplified, which is not indicative of prostate cancer metastases. However, if the band is somewhat smaller, a 567 base pair product, the indication is that the PSR mRNA is amplified by PCR and cells, other than the prostate, are activley transcribing PSR protein and are circulating in the blood, i.e. metastisizing. All specimens are analyzed at least twice to confirm a positive or negative outcome.

Verification of the nucleotide sequence of the PCR products is done by microsequencing. The PCR product is purified with a Qiagen PCR Product Purification Kit (Qiagen, Chatsworth, Calif.) as described by the manufacturer. One µg of the PCR product undergoes PCR sequencing by using the Taq DyeDeoxy Terminator Cycle sequencing kit in a Perkin-Elmer 9600 PCR machine as described by Applied Biosystems (Foster, Calif.). The sequenced product is purified using Centri-Sep columns (Princeton Separations, Adelphia, N.J.) as described by the company. This product is then analyzed with an ABI model 373A DNA sequencing system (Applied Biosystems) integrated with a Macintosh IIci computer.

EXAMPLE 2

Bacterial Expression and Purification of PSR

The DNA sequence encoding PSR, ATCC # 75913, is initially amplified using PCR oligonucleotide primers corresponding to the 5' sequences of the processed protein (minus the signal peptide sequence) and the vector sequences 3' to the PSR gene. Additional nucleotides corresponding to PSR are added to the 5' and 3' sequences respectively. The 5' oligonucleotide primer has the sequence 5 GATCGATGTCGAC CTGTCCAGTGGGGTGTGTAC (SEQ ID No. 5) 3' contains a SalI restriction enzyme site followed by 20 nucleotides of PSR coding sequence starting from amino acid 10. The 3' sequence 5' ATCGATCTCTA-GATTATGTTAGTCTATTGGGAGGCCC 3' (SEQ ID No. 6) contains complementary sequences to an XbaI site and is followed by 23 nucleotides of PSR coding sequence. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance ($Amp^r$) a bacterial origin of replication (ori), an IPTG-regulatable promoter operator (P/O), a ribosome binding site (RBS), a 6-His tag and restriction enzyme sites. pQE-9 is then digested with SalI and XbaI. The amplified sequences are ligated into pQE-9 and are inserted in frame with the sequence encoding for the histidine tag and the RBS. The ligation mixture is then used to transform E. coli strain m15/pREP4 available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the laci repressor and also confers kanamycin resistance ($Kan^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG ("Isopropyl-B-D-thiogalacto pyranoside") is then added to a final concentration of 1 mM. IPTG induces by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized PSR is purified from this solution by chromatography on a Nickel-Chelate column under conditions that allow for tight binding by proteins containing the 6-His tag (Hochuli, E. et al., J. Chromatography 411:177–184 (1984)). PSR ( 90% pure) is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 3

Expression of Recombinant PSR in COS cells

The expression of plasmid, PSR HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire PSR precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding PSR, ATCC # 75913, is constructed by PCR on the original full-length PSR clone using two primers: the 5' primer 5' GATCGAAGTCC TTC-CTTCTGTATATGGCTG 3' (SEQ ID No. 7) contains a HindIII site followed by 19 nucleotides of PSR coding sequence starting from the initiation codon; the 3' sequence 5'   C G C T C T A G A T C A A G C G T A G T C T G G-

GACGTCGTATGGGTATTGGGAGGCCCAGCAGGT3' (SEQ ID No. 8) contains complementary sequences to an XbaI site, translation stop codon, HA tag and the last 18 nucleotides of the PSR coding sequence (not including the stop codon). Therefore, the PCR product contains a HindIII site, PSR coding sequence followed by HA tag fused in frame, a translation termination stop codon next to the HA tag, and an XbaI site. The PCR amplified DNA fragment and the vector, pcDNAI/Amp, are digested with HindIII and XbaI restriction enzyme and ligated. The ligation mixture is transformed into E. coli strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant PSR, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the PSR HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}S$ -cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4

Expression Pattern of PSR in human tissue

Northern blot analysis is carried out to examine the levels of expression of PSR in human tissues. Total cellular RNA samples are isolated with RNAzol™ B system (Biotecx Laboratories, Inc. Houston, Tex.). About 10 µg of total RNA isolated from each human tissue specified is separated on 1% agarose gel and blotted onto a nylon filter. (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column. (5 Prime −3 Prime, Inc. Boulder, Colo.). The filter is then hybridized with radioactive labeled full length PSR gene at 1,000,000 cpm/ml in 0.5 M $NaPO_4$, pH 7.4 and 7% SDS overnight at 65° C. After wash twice at room temperature and twice at 60° C. with 0.5×SSC, 0.1% SDS, the filter is then exposed at −70° C. overnight with an intensifying screen (See Table 1).

Numerous modifications and variations of the present invention are possible in light of the above teachings and, therefore, within the scope of the appended claims, the invention may be practiced otherwise than as particularly described.

What is claimed is:

1. An isolated polypeptide comprising a polypeptide selected from the group consisting of:
   (a) a polypeptide consisting of amino acids 1 to 316 of SEQ ID NO:2;
   (b) a polypeptide consisting of amino acids 2 to 316 of SEQ ID NO:2;
   (c) a polypeptide encoded by a polynucleotide which hybridizes with the complement of the coding portion of the polynucleotide of SEQ ID NO:1, wherein said polypeptide binds an antibody specific for the polypeptide of (a), wherein said antibody is produced by direct injection of the polypeptide of (a) into an animal, and wherein said hybridization takes place under hybridization conditions comprising hybridization in a buffer consisting of 0.5M NaPO$_4$, pH 7.4 and 7% SDS at 65° C. and wash in a buffer consisting of 0.5×SSC 0.1% SDS at 60° C.; and
   (d) a fragment of the polypeptide of (a) which binds an antibody specific for the polypeptide of (a) and wherein said antibody is produced by direct injection of the polypeptide of (a) into an animal.

2. The isolated polypeptide of claim 1 which comprises polypeptide (a).

3. The isolated polypeptide of claim 1 which comprises polypeptide (b).

4. The isolated polypeptide of claim 1 which comprises polypeptide (c).

5. The isolated polypeptide of claim 1 which comprises polypeptide (d).

6. An isolated polypeptide comprising a polypeptide selected from the group consisting of:
   (a) the full-length polypeptide encoded by the human cDNA contained in ATCC Deposit No. 75913;
   (b) the full-length polypeptide encoded by the human cDNA contained in ATCC Deposit No. 75913, excepting the N-terminal methionine;
   (c) a polypeptide encoded by a polynucleotide which hybridizes to the human cDNA insert contained in ATCC Deposit No. 75913, wherein said polypeptide binds an antibody specific for the polypeptide of (a), wherein said antibody is produced by direct injection of the polypeptide of (a) into an animal, and wherein said hybridization takes place under hybridization conditions comprising hybridization in a buffer consisting of 0.5M NaPO4, pH 7.4 and 7% SDS at 65° C. and wash in a buffer consisting of 0.5×SSC 0.1 % SDS at 60° C.; and
   (d) a fragment of the polypeptide of (a) which binds to an antibody specific for the polypeptide of (a) and wherein said antibody is produced by direct injection of the polypeptide of (a) into an animal.

7. The isolated polypeptide of claim 6, which comprises polypeptide (a).

8. The isolated polypeptide of claim 6 which comprises polypeptide (b).

9. The isolated polypeptide of claim 6 which comprises polypeptide (c).

10. The isolated polypeptide of claim 6 which comprises polypeptide (d).

11. A composition comprising the polypeptide of claim 1 in a pharmaceutically acceptable carrier.

12. A composition comprising the polypeptide of claim 6 in a pharmaceutically acceptable carrier.

13. An isolated polypeptide according to claim 1, wherein said isolated polypeptide is produced from a host cell transformed with a polynucleotide which encodes said isolated polypeptide.

14. An isolated polypeptide according to claim 6, wherein said isolated polypeptide is produced from a host cell transformed with a polynucleotide which encodes said isolated polypeptide.

15. The isolated polypeptide of claim 1, which further comprises a heterologous polypeptide.

16. The isolated polypeptide of claim 6, which further comprises a heterologous polypeptide.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1086 BASE PAIRS
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO:1:

```
CCGGCAGAGA TGGTTGAGCT CATGTTCCCG CTGTTGCTCC TCCTTCTGCC CTTCCTTCTG      60

TATATGGCTG CGCCCCAAAT CAGGAAAATG CTGTCCAGTG GGGTGTGTAC ATCAACTGTT     120

CAGCTTCCTG GGAAAGTAGT TGTGGTCACA GGAGCTAATA CAGGTATCGG GAAGGAGACA     180

GCCAAAGAGC TGGCTCAGAG AGGAGCTCGA GTATATTTAG CTTGCCGGGA TGTGGAAAAG     240

GGGGAATTGG TGGCCAAAGA GATCCAGACC ACGACAGGGA ACCAGCAGGT GTTGGTGCGG     300

AAACTGGACC TGTCTGATAC TAAGTCTATT CGAGCTTGGG CTAAGGGCTT CTTAGCTGAG     360

GAAAAGCACC TCCACGTTTG GATCAACAAT GCAGGAGTGA TGATGTGTCC GTACTCGAAG     420

ACAGCAGATG GCTTTGAGAT GCACATAGGA GTCAACCACT TGGGTCACTT CCTCCTAACC     480

CATCTGCTGC TAGAGAAACT AAAGGAATCA GCCCCATCAA GGATAGTAAA TGTGTCTTCC     540

CTCGCACATC ACCTGGGAAG GATCCACTTC CATAACCTGC AGGGCGAGAA ATTCTACAAT     600

GCAGGCCTGG CCTACTGTCA CAGCAAGCTA GCCAACATCC TCTTCACCCA GGAACTGGCC     660
```

```
CGGAGACTAA AAGGCTCTGG CGTTACGACG TATTCTGTAC ACCCTGGCAC AGTCCAATCT      720

GAACTGGTTC GGCACTCATC TTTCATGAGA TGGATGTGGT GGCTTTTCTC CTTTTTCATC      780

AAGACTCCTC AGCAGGGAGC CCAGACCAGG CTGCACTGTG CCTTAACAGA AGGTCTTGAG      840

ATTCTAAGTG GAATCATTT CAGTGACTGT CATGTGGCAT GGGTCTCTGC CCAAGCTCGT       900

AATGAGACTA TAGCAAGGCG GCTGTGGGAC GTCATTGTGA CCTGCTGGGC CTCCCAATAG      960

ACTAACAGGC AGTGCCAGTT GGACCCAAGA GAAGACTGCA GCAGACTACA CAGTACTTCT      1020

TGTCAAAATG ATTCTCCTTC AAGGTTTTCA AAACCTTTAG CACAAAGAGA GCAAAACCTT      1080

CCAGCC                                                                 1086
```

(2) INFORMATION FOR SEQ ID NO:2:

(i) SEQUENCE CHARACTERISTICS:
        (A) LENGTH: 316 AMINO ACIDS
        (B) TYPE: AMINO ACID
        (C) STRANDEDNESS:
        (D) TOPOLOGY: LINEAR (ii) MOLECULE TYPE: PROTEIN (xi) SEQUENCE DESCRIPTION: SEQ ID NO:2:

```
Met Val Glu Leu Met Phe Pro Leu Leu Leu Leu Leu Pro Phe
              5                  10                  15

Leu Leu Tyr Met Ala Ala Pro Gln Ile Arg Lys Met Leu Ser Ser
             20                  25                  30

Gly Val Cys Thr Ser Thr Val Gln Leu Pro Gly Lys Val Val Val
             35                  40                  45

Val Thr Gly Ala Asn Thr Gly Ile Gly Lys Glu Thr Ala Lys Glu
             50                  55                  60

Leu Ala Gln Arg Gly Ala Arg Val Tyr Leu Ala Cys Arg Asp Val
             65                  70                  75

Glu Lys Gly Glu Leu VAl Ala Lys Glu Ile Gln Thr Thr Thr Gly
             80                  85                  90

Asn Gln Gln Val Leu Val Arg Lys Leu Asp Leu Ser Asp Thr Lys
             95                 100                 105

Ser Ile Arg Ala Trp Ala Lys Gly Phe Lys Ala Glu Glu Lys His
            110                 115                 120

Leu His Val Trp Ile Asn Asn Ala Gly Val Met Met Cys Pro Tyr
            125                 130                 135

Ser Lys Thr Ala Asp Gly Phe Glu Met His Ile Gly Val Asn His
            140                 145                 150

Leu Gly His Phe Leu Leu Thr His Leu Leu Glu Lys Leu Lys
            155                 160                 165

Glu Ser Ala Pro Ser Arg Ile Val Asn Val Ser Ser Leu Ala His
            170                 175                 180

His Leu Gly Arg Ile His Phe His Asn Leu Gln Gly Glu Lys Phe
            185                 190                 195

Tyr Asn Ala Gly Leu Ala Tyr Cys His Ser Lys Leu Ala Asn Ile
            200                 205                 210

Leu Phe Thr Gln Glu Leu Ala Arg Arg Leu Lys Gly Ser Gly Val
            215                 220                 225

Thr Thr Tyr Ser Val His Pro Gly Thr Val Gln Ser Glu Leu Val
            230                 235                 240

Arg His Ser Ser Phe Met Arg Trp Met Trp Trp Leu Phe Ser Phe
            245                 250                 255
```

-continued

```
Phe Ile Lys Thr Pro Gln Gln Gly Ala Gln Thr Arg Leu His Cys
            260                 265                 270

Ala Leu Thr Glu Gly Leu Glu Ile Leu Ser Gly Asn His Phe Ser
            275                 280                 285

Asp Cys His Val Ala Trp Val Ser Ala Gln Ala Arg Asn Glu Thr
            290                 295                 300

Ile Ala Arg Arg Leu Trp Asp Val Ile Val Thr Cys Trp Ala Ser
            305                 310                 315

Gln
```

(2) INFORMATION FOR SEQ ID NO:3:

(i) SEQUENCE CHARACTERISTICS:
        (A) LENGTH: 22 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

AAGAGATCCA GACCACGACA GG                                    22

(2) INFORMATION FOR SEQ ID NO:4:

(i) SEQUENCE CHARACTERISTICS:
        (A) LENGTH: 22 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

AAGGCACAGT GCAGCCTGGT CT                                    22

(2) INFORMATION FOR SEQ ID NO:5:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:5:

GATCGATGTC GACCTGTCCA GTGGGGTGTG TAC                          33

(2) INFORMATION FOR SEQ ID NO:6:

(i) SEQUENCE CHARACTERISTICS:
        (A) LENGTH: 37 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:6:

ATCGATCTCT AGATTATGTT AGTCTATTGG GAGGCCC                   37

(2) INFORMATION FOR SEQ ID NO:7:

(i) SEQUENCE CHARACTERISTICS:

```
           (A) LENGTH:  30 BASE PAIRS
           (B) TYPE:  NUCLEIC ACID
           (C) STRANDEDNESS:  SINGLE
           (D) TOPOLOGY:  LINEAR (ii) MOLECULE TYPE:  Oligonucleotide (xi) SEQUENCE DESCRIPTION:  SEQ ID NO:7:

GATCGAAGTC CTTCCTTCTG TATATGGCTG                                     30

(2) INFORMATION FOR SEQ ID NO:8:

(i) SEQUENCE CHARACTERISTICS:
           (A) LENGTH:  57 BASE PAIRS
           (B) TYPE:  NUCLEIC ACID
           (C) STRANDEDNESS:  SINGLE
           (D) TOPOLOGY:  LINEAR (ii) MOLECULE TYPE:  Oligonucleotide (xi) SEQUENCE DESCRIPTION:  SEQ ID NO:8:

CGCTCTAGAT CAAGCGTAGT CTGGGACGTC GTATGGGTAT TGGGAGGCCC AGCAGGT       57
```